US006605737B1

(12) United States Patent
Nakamura et al.

(10) Patent No.: US 6,605,737 B1
(45) Date of Patent: Aug. 12, 2003

(54) PROCESS FOR THE PREPARATION OF CONDENSED PHOSPHORIC ACID ESTERS

(75) Inventors: Shin Nakamura, Handa (JP); Taku Fujisawa, Handa (JP); Takafumi Okawa, Handa (JP)

(73) Assignee: Daihachi Chemical Industry Co., Ltd., Osaka (JP)

( * ) Notice: Subject to any disclaimer, the term of this patent is extended or adjusted under 35 U.S.C. 154(b) by 0 days.

(21) Appl. No.: 10/129,204

(22) PCT Filed: May 30, 2000

(86) PCT No.: PCT/JP00/03481

§ 371 (c)(1),
(2), (4) Date: May 3, 2002

(87) PCT Pub. No.: WO01/34616

PCT Pub. Date: May 17, 2001

(30) Foreign Application Priority Data

Nov. 5, 1999 (JP) .......................................... 11-316022

(51) Int. Cl.$^7$ ................................................. C07F 9/02
(52) U.S. Cl. .......................................... 558/92; 568/700
(58) Field of Search ............................. 558/92; 568/700

(56) References Cited

U.S. PATENT DOCUMENTS 6,388,120 B1 * 5/2002 Farner et al. ................. 558/92

* cited by examiner

*Primary Examiner*—Joseph K. McKane
*Assistant Examiner*—Robert Shiao
(74) *Attorney, Agent, or Firm*—Snell & Wilmer, LLP

(57) ABSTRACT

An objective of the present invention is to provide a method for preparing a high-purity, condensed phosphoric ester made of a bisphenol A derivative and having a very low content of monomer-type phosphoric ester that causes reduction in the heat resistance and the contamination of the molds during the molding when the condensed phosphoric ester is used as an additive for a resin.

According to the present invention, a bisphenol A derivative, a phosphorus oxytrihalide and a hydroxy compound are reacted in the presence of a decomposition retardant, whereby the above problems can be solved.

12 Claims, No Drawings

PROCESS FOR THE PREPARATION OF CONDENSED PHOSPHORIC ACID ESTERS

TECHNICAL FIELD

The present invention relates to a method for preparing a condensed phosphoric ester. More specifically, the present invention relates to a method for preparing a condensed phosphoric ester which has a low content of volatile components that cause an adverse influence in the quality of resins, and which is excellent as an additive for resins, such as a plasticizer, a flame retardant, or the like.

BACKGROUND ART

Conventional Art

Conventionally, various types of flame retardants are used for flame retardation of inflammable plastic materials, for example, halogen compounds such as decabromobiphenylether and tetrabromobisphenol A, and low molecular weight phosphorus compounds such as cresyl diphenyl phosphate and triphenyl phosphate.

Today, resin compositions are required to be non-halogenic from an environmental point of view, for example, due to the hazardous effects of dioxin. Flame retardants containing heavy metals cause problems due to their toxicity. Under these circumstances, phosphorus-based flame retardants have now become a target of attention. Among the phosphorus-based flame retardants, aromatic phosphoric ester-based flame retardants are a target of attention for their effectiveness especially in the applications of engineering plastics such as PC/ABS alloys and modified PPE since they have little adverse influence on the environment as well as superb physical properties. Actually, the industrial demand for phosphorus-based flame retardants, especially aromatic phosphoric ester-based flame retardants, is good and continues to increase at a high rate.

However, engineering plastics are molded at a very high temperature and therefore the following problems have occurred. When a low molecular weight monomer-type phosphoric ester such as triphenyl phosphate (TPP) or tricresyl phosphate (TCP) is used, the monomer-type phosphoric ester is thermally decomposed, bleeds out or volatizes during the molding process, which causes defective molding, contamination of the molds or the like.

It is known that use of a high molecular weight condensed phosphoric ester as a flame retardant is effective for avoiding these problems. Especially, it is known that use of a condensed phosphoric ester, which has a low content of a low molecular weight monomer-type phosphoric ester, as a flame retardant is effective for avoiding these problems.

In general, a condensed phosphoric ester is prepared by reacting phosphorus oxychloride with a divalent hydroxy compound, such as hydroquinone, resorcin, bisphenol A, or the like, and a monovalent hydroxy compound, such as phenol, cresol, or the like.

However, in the case of a condensed phosphoric ester prepared by a conventional method using a bisphenol A derivative as the divalent hydroxy compound, the following problems have been pointed out. When such a condensed phosphoric ester is mixed with a resin, a molded product is colored, and heat resistance and moldability are adversely influenced.

Problems to be Solved by the Invention

An objective of the present invention is to solve the above-described problems. That is, an objective of the present invention is to provide a method for preparing a condensed phosphoric ester formed from a bisphenol A derivative as a starting material, which does not give a color on a molded product or adversely influence heat resistance and moldability even when mixed with a resin. Another objective of the present invention is to enhance the quality of resin-molded products by using the condensed phosphoric ester produced by a method according to the present invention as a flame retardant, so as to make a contribution to the society.

DISCLOSURE OF THE INVENTION

Means for Solving the Problems

As a result of active studies, the present inventors found that, in a reaction of a bisphenol A derivative with a phosphorus oxytrihalide and a hydroxy compound, the bisphenol A derivative comes into contact with hydrogen halide generated in the reaction with the bisphenol A derivative so as to decompose the bisphenol A derivative, whereby generation of an aryl group-containing phosphate and an isopropenyl aryl group-containing phosphate (monomer-type phosphoric ester) is caused. The present inventors further found that, when the above reaction occurs in the presence of a decomposition retardant, generation of monomer-type phosphoric ester is suppressed, whereby the above-described problems can be solved. Thus, the present inventors completed the present invention.

It should be noted that, in the present specification, an isopropenyl aryl group-containing phosphate is abbreviated as an "IPP".

Specifically, a method for preparing a condensed phosphoric ester according to the present invention includes a process of reacting a bisphenol A derivative, a phosphorus oxytrihalide, and a hydroxy compound in the presence of a decomposition retardant.

In one embodiment, the decomposition retardant is an organic carboxylic acid-based compound.

In one embodiment, the organic carboxylic acid-based compound is ascorbic acid or adipic acid.

In one embodiment, the decomposition retardant is an oxide or chloride of tin, copper, or iron.

In one embodiment, the oxide or chloride of tin, copper, or iron is a stannic oxide, a ferric chloride, or a cupric chloride.

In one embodiment, the amount of the decomposition retardant used is 0.01–5 parts by weight with respect to 100 parts by weight of the bisphenol A derivative.

In one embodiment, the process of reacting a bisphenol A derivative, a phosphorus oxytrihalide, and a hydroxy compound includes:

a first step of reacting the bisphenol A derivative and the phosphorus oxytrihalide so as to produce a phosphorohalidate; and a second step of reacting the phosphorohalidate and the hydroxy compound.

In one embodiment, the process of reacting a bisphenol A derivative, a phosphorus oxytrihalide, and a hydroxy compound includes:

a first step of reacting the bisphenol A derivative and the phosphorus oxytrihalide so as to produce a phosphorohalidate, and removing unreacted phosphorus oxytrihalide from a reaction product; and a second step of reacting the phosphorohalidate and the hydroxy compound.

In one embodiment, the amount of the hydroxy compound used is greater by equal to or less than 2 mol % than an amount which is theoretically necessary for turning the entire amount of the phosphorohalidate into a condensed phosphoric ester.

In one embodiment, the process of reacting a bisphenol A derivative, a phosphorus oxytrihalide, and a hydroxy compound includes:
  a first step of reacting the bisphenol A derivative and the phosphorus oxytrihalide so as to produce a phosphorohalidate; and
  a second step of reacting a reaction product obtained at the first step and a monophenol-based compound at the temperature of 120° C. or lower, and thereafter, increasing the temperature to 120° C. or higher, and reacting the phosphorohalidate and a hydroxy compound.

In one embodiment, the process of reacting a bisphenol A derivative, a phosphorus oxytrihalide, and a hydroxy compound includes:
  a first step of reacting the bisphenol A derivative and the phosphorus oxytrihalide so as to produce a phosphorohalidate, and removing unreacted phosphorus oxytrihalide from a reaction product; and
  a second step of reacting a reaction product obtained at the first step and a monophenol-based compound at the temperature of 120° C. or lower, and thereafter, increasing the temperature to 120° C. or higher, and reacting the phosphorohalidate and a hydroxy compound.

In one embodiment, the condensed phosphoric ester is 2,2-bis{4-[bis(phenoxy)phosphoryl]oxyphenyl}propane.

BEST MODE FOR CARRYING OUT THE INVENTION

Embodiments of the Invention

Hereinafter, the present invention will be specifically described, but the extent of the present invention is not limited to the following.

Examples of a process for preparing a condensed phosphoric ester of the present invention can generally be classified into the following three processes:

1. a process where a first step of reacting a bisphenol A derivative with a phosphorus oxytrihalide in the presence of a decomposition retardant is performed, and thereafter, a second step of reacting a reaction product obtained after the first step with a hydroxy compound is performed;
2. a process where a first step of reacting a phosphorus oxytrihalide with a hydroxy compound in the presence of a decomposition retardant is performed, and thereafter, a second step of reacting a reaction product obtained after the first step with a bisphenol A derivative; and
3. a process where a bisphenol A derivative, a phosphorus oxytrihalide, and a hydroxy compound are simultaneously brought into reaction in the presence of a decomposition retardant.

Among these processes, above process 1 is preferable in respect that a volatile monomer-type phosphoric ester can be efficiently reduced.

First, above process 1 is described.

Process 1 includes a first step and a second step, which will be described below.

First Step of Process 1

At the first step of process 1, a bisphenol A derivative and a phosphorus oxytrihalide are reacted in the presence of a decomposition retardant so as to obtain a phosphorohalidate.

In the present invention, the decomposition retardant refers to a compound which has a function of suppressing decomposition of a bisphenol A derivative by a hydrogen halide. Preferable examples of such a compound include: organic carboxylic acid-based compounds; compounds containing any of tin, copper, and iron; and the like.

The organic carboxylic acid-based compound refers to an organic carboxylic acid and a salt thereof. An organic carboxylic acid is preferable. Specifically, examples of the organic carboxylic acid include ascorbic acid, terephthalic acid, malic acid, adipic acid, sebacic acid, azelaic acid, oxalic acid, citric acid, zinc stearate, magnesium stearate, and the like. Preferably, the organic carboxylic acid is ascorbic acid or adipic acid.

The compounds containing any of tin, copper, and iron preferably refer to oxides and chlorides of tin, copper, or iron. Specifically, examples of such a compound include a stannic oxide, cupric chloride, ferric chloride, and the like. More preferably, such a compound is a stannic oxide.

These decomposition retardants suppress decomposition reaction of a bisphenol A derivative by a hydrogen halide. Thus, in the preparation of a condensed phosphoric ester, by-production of a monomer-type phosphoric ester can be suppressed.

A decomposition retardant may be solely used. Alternatively, two or more types of decomposition retardants may be used together.

The amount of the decomposition retardant used is preferably 0.01–5 parts by weight, more preferably 0.1–2 parts by weight, and still more preferably 0.15–1.5 parts by weight with respect to 100 parts by weight of a bisphenol A derivative. In the case where the amount of the decomposition retardant is too small, the decomposition retarding effect becomes small, and it becomes difficult to obtain a sufficient decomposition retarding effect. In the case where the amount of the decomposition retardant is too large, the decomposition retardant is likely to remain in the product as an impurity.

The decomposition retardant can be added at any time during preparation of a condensed phosphoric ester. However, it is preferable to add the decomposition retardant before a reaction of a bisphenol A derivative and a phosphorus oxytrihalide because the decomposition retardant suppresses a reaction of a bisphenol A derivative and hydrogen halide.

The decomposition retardant may not be removed after preparation of a condensed phosphoric ester so as to be left in a condensed phosphoric ester product. However, in the case where in view of the quality of an intended condensed phosphoric ester product, the decomposition retardant should not be left in the condensed phosphoric ester product, or the amount of the decomposition retardant left in the condensed phosphoric ester product should be equal to or smaller than a certain amount, a step of removing the decomposition retardant may be provided. In this case, a method for removing the decomposition retardant is realized by any method. For example, filtration, decantation, orthe like, may be employed. The preferable time for removing the decomposition retardant is the time after the reaction of a phosphorohalidate and a hydroxy compound has been completed.

Examples of the phosphorus oxytrihalide include phosphorus oxychloride and phosphorus oxybromide.

The bisphenol A derivative refers to bisphenol A or a derivative thereof, which is represented by the following formula (A):

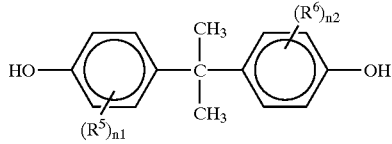

(A)

(where $R^5$ and $R^6$ are the same or different from each other and represent an alkyl group containing 1 to 3 carbon atoms; and n1 and n2 each represent an integer from 0 to 4).

In the present invention, a phosphorohalidate refers to a compound represented by the following formula (I):

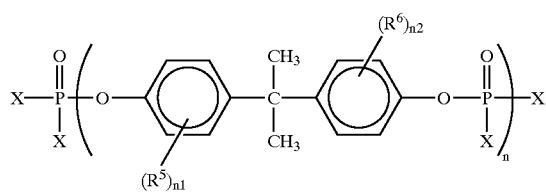

(I)

(where X represents a halogen atom; n represents an integer from 1 to 10: and $R^5$, $R^6$, n1 and n2 each refer to the same as above.)

According to conventional, general technical knowledge about the amount of the phosphorus oxytrihalide and the bisphenol A derivative used, it is considered to be non-preferable that the amount of the phosphorus oxytrihalide is greater than a stoichiometrical reaction amount which is calculated from the amount of the bisphenol-based compound (i.e., 2 mol times the amount of the bisphenol-based compound). The reason is that the amount of remaining unreacted phosphorus oxytrihalide necessarily increases, which complicates the operation for recovering the unreacted phosphorus oxytrihalide. However, when the amount of the phosphorus oxytrihalide used is equal to or greater than 4.5 mol times, more preferably equal to or greater than 5 mol times, and still more preferably equal to or greater than 5.4 mol times the amount of the bisphenol A derivative, an advantage that the decomposition of the bisphenol A derivative is suppressed is expected.

Thus, in the present invention, the amount of the phosphorus oxytrihalide and the bisphenol A derivative are not limited to a specific amount. However, for the above-described reasons, the amount of the phosphorus oxytrihalide is preferably determined so as to be equal to or greater than 4.5 mol times, more preferably equal to or greater than 5 mol times, and still more preferably equal to or greater than 5.4 mol times the amount of the bisphenol A derivative.

Here, "mol times" refers to the ratio based on the mol value.

The upper limit of the amount of the phosphorus oxytrihalide cannot be determined. When the amount of the phosphorus oxytrihalide is excessive, the operation efficiency in the reactor and also the productivity are likely to be decreased. The phosphorus oxytrihalide is usually preferably used in an amount equal to or less than 8 mol times, and more preferably equal to or less than 6 mol times the amount of the bisphenol-based compound. Still more preferably, the amount of the phosphorus oxytrihalide and the bisphenol A derivative are adjusted within the above-mentioned ranges so that the concentration of the hydrogen halide in the reaction solution is equal to or less than 5% by weight.

According to the present invention, a catalyst can be used. Usable catalysts include, for example, Lewis acid-based catalysts such as aluminum chloride, magnesium chloride and titanium tetrachloride or the like.

The other reaction conditions, for example, the reaction temperature, reaction time and reduction in pressure can be appropriately selected in accordance with the type and condensation degree of the intended condensed phosphoric ester, and type and scale of the apparatus used. The temperature selected in the first step of process 1 is preferably 80 to 130° C. It is acceptable to start with a temperature lower than 80° C. and then raise the temperature to 80 to 130° C. For example, it is acceptable to start with room temperature and then raise the temperature to 80 to 130° C. The reaction time selected in the first step of process 1 is preferably 3 to 20 hours. Hydrogen halide gas generated during the reaction is preferably captured by water.

An organic solvent can be used when necessary although it is not usually necessary. For example, aromatic group-based organic solvents including toluene, xylene, and dichlorobenzene and aliphatic group-based organic solvents including hexane and heptane are usable.

When it is necessary to prevent the resultant product from being colored, a phosphorus-based compound such as, for example, triphenyl phosphate or tris(2,6-di-t-butyl) phosphate; a hindered phenol-based compound such as, for example, 2,6-di-t-butyl-p-cresol (BHT) or 2-methyl-6-t-butyl-p-cresol: or the like can be added as a coloring prevention agent.

Removal of Remaining Phosphorus Oxytrihalide

At the first step of process 1, it is preferable to perform an operation for removing the phosphorus oxytrihalide remaining unreacted after the reaction of the bisphenol A derivative and the phosphorus oxytrihalide.

The removal of the phosphorus oxyhalide can be performed using any conventionally known method.

The removal of the unreacted phosphorus oxytrihalide is usually performed at normal pressure or under reduced pressure. If the second step of process 1 described below is performed in the state where the phosphorus oxytrihalide is not sufficiently removed, i.e., in the state where phosphorus oxytrihalide remains, a monomer-type phosphoric ester is likely to be generated. Therefore, it is preferable to remove and recover the maximum possible amount of the phosphorus oxytrihalide. Preferable conditions for removing and recovering the phosphorus oxytrihalide are, for example, as follows. The pressure is reduced to preferably equal to or less than 200 mmHg, more preferably equal to or less than 100 mmHg, and still more preferably equal to or less than 50 mmHg, by a vacuum pump. The recovery temperature is preferably 100 to 200° C., more preferably 100 to 170° C., and still more preferably 100 to 150° C.

More specifically, it is desirable that the phosphorus oxytrihalide is removed and recovered at 90 to 130° C. while the pressure is reduced to 5 to 20 mmHg by a vacuum pump, for example.

In the reaction product after the first step of process 1, a part of the IPP produced as a by-product in the first step of process 1 usually remains. After the first step of process 1, operations for removing only the residual IPP, for example purification by chromatography, can be performed. However, the method according to the present invention allows the second step to be performed without conducting any specific operation for removing only the IPP.

Second Step of Process 1

At the second step of process 1, the phosphorohalidate obtained as described above and a hydroxy compound are reacted in order to prepare a condensed phosphoric ester.

In the present invention, the condensed phosphoric ester refers to a phosphoric ester which is obtained by reacting a phosphorus oxytrihalide having two phosphorus atoms in one molecule thereof, a hydroxy compound, and the bisphenol A derivative. Preferable examples of the condensed phosphoric ester include a compound represented by the following formula (II):

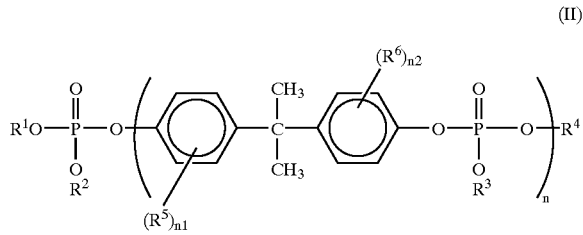

(where $R^1$, $R^2$, $R^3$ and $R^4$ represent an identical or different aryl group containing 6 to 15 carbon atoms; and $R^5$, $R^6$, n1, n2 and n represent the same as above.)

Examples of the aryl group containing 6 to 15 carbon atoms include phenyl, (o-, m-, p-)methylphenyl, (o-, m-, p-)ethylphenyl, (o-, m-, p-)n-propylphenyl, (o-, m-, p-)isopropylphenyl, (o-, m-, p-)n-butylphenyl, (o-, m-, p-)sec-butylphenyl, (o-, m-, p-)tert-butylphenyl, (2,3-2,4-, 2,5-, 2,6-, 3,4-, 3,5-)dimethylphenyl, (2,3-2,4-, 2,5-, 2,6-, 3,4-, 3,5-)diethylphenyl, 2-methyl-3-ethylphenyl, 2-methyl-4-ethylphenyl, 2-methyl-5-ethylphenyl, 2-methyl-6-ethylphenyl, 3-methyl-4-ethylphenyl, 3-methyl-5-ethylphenyl, 2-ethyl-3-methylphenyl, 2-ethyl-4-methylphenyl, 2-ethyl-5-methylphenyl, 3-ethyl-4-methylphenyl, (2,3-, 2,4-, 2,5-, 2,6-, 3,4-, 3,5-)di-n-propylphenyl, (2,3-, 2,4-, 2,5-, 2,6-, 3,4-, 3,5-)diisopropylphenyl, (2,3-, 2,4-, 2,5-, 2,6-, 3,4-, 3,5-)di-n-butylphenyl, (2,3-, 2,4-, 2,5-, 2,6-, 3,4-, 3,5-)di-sec-butylphenyl, (2,3-, 2,4-, 2,5-, 2,6-, 3,4-, 3,5-)di-tert-butylphenyl, (2,3,6-, 2,3,5-, 2,3,4-, 2,4,5-, 2,4,6-, 3,4,5-)trimethylphenyl, (2,3,6-, 2,3,5-, 2,3,4-, 2,4,5-, 2,4,6-, 3,4,5-)triethylphenyl, (2,3,6-, 2,3,5-, 2,3,4-, 2,4,5-, 2,4,6-, 3,4,5-)tripropylphenyl, and naphtyl. Here, "(o-, m-, p-)" indicates that substituents independently exist in either positions of o-(ortho), m-(meta) or p-(para) on a benzene ring. "(2,3-, 2,4-, 2,5-, 2,6-, 3,4-, 3,5-)" indicates that substituents independently exist in positions 2,3-, 2,4-, 2,5-, 2,6-, 3,4-, or 3,5- on a benzene ring. "(2,3,6-, 2,3,5-, 2,3,4-, 2,4,5-, 2,4,6-, 3,4,5-)" indicates that substituents independently exist in positions 2,3,6-, 2,3,5-, 2,3,4-, 2,4,5-, 2,4,6-, or 3,4,5- on a benzene ring.

Preferable specific examples of the condensed phosphoric ester represented by formula (II) include 2,2-bis{4-[bis(phenoxy)phosphoryl]oxyphenyl}propane, 2,2-bis{4-[bis(methylphenoxy)phosphoryl]oxyphenyl}propane, 2,2-bis{4-[bis(dimethylphenoxy)phosphoryl]oxyphenyl}propane, and 2,2-bis{4-[bis(methylethylphenoxy)phosphoryl]oxyphenyl}propane which are made from a bisphenol A.

Examples of the hydroxy compound include phenol, (o-, m-, p-)methylphenol, (o-, m-, p-)ethylphenol, (o-, m-, p-)n-propylphenol, (o-, m-, p-)isopropylphenol, (o-, m-, p-)n-butylphenol, (o-, m-, p-)sec-butylphenol, (o-, m-, p-)tert-butylphenol, (o-, m-, p-)methylphenol, (2,3-2,4-, 2,5-, 2,6-, 3,4-, 3,5-)dimethylphenol, (2,3-2,4-, 2,5-, 2,6-, 3,4-, 3,5-)diethylphenol, 2-methyl-3-ethylphenol, 2-methyl-4-ethylphenol, 2-methyl-5-ethylphenol, 2-methyl-6-ethylphenol, 3-methyl-4-ethylphenol, 3-methyl-5-ethylphenol, 2-ethyl-3-methylphenol, 2-ethyl-4-methylphenol, 2-ethyl-5-methylphenol, 3-ethyl-4-methylphenol, (2,3-, 2,4-, 2,5-, 2,6-, 3,4-, 3,5-)di-n-propylphenol, (2,3-, 2,4-, 2,5-, 2,6-, 3,4-, 3,5-)diisopropylphenol, (2,3-, 2,4-, 2,5-, 2,6-, 3,4-, 3,5-)di-n-butylphenol, (2,3-, 2,4-, 2,5-, 2,6-, 3,4-, 3,5-)di-sec-butylphenol, (2,3-, 2,4-, 2,5-, 2,6-, 3,4-, 3,5-)di-tert-butylphenol, (2,3,6-, 2,3,5-, 2,3,4-, 2,4,5-, 2,4,6-, 3,4,5-)trimethylphenol, (2,3,6-, 2,3,5-, 2,3,4-, 2,4,5-, 2,4,6-, 3,4,5-)triethylphenol, (2,3,6-, 2,3,5-, 2,3,4-, 2,4,5-, 2,4,6-, 3,4,5-)tripropylphenol, and naphtol. Phenol is especially preferable. One hydroxy compound or a combination of two or more hydroxy compounds can be used.

In the present invention, a monomer-type phosphoric ester is a phosphoric ester having one phosphorus atom in a molecule thereof, and is a generic name for:

① triesters of phosphoric acid generated by a reaction of a decomposition product of a bisphenol A derivative and a phosphorus oxytrihalide: and ② triesters of phosphoric acid generated by a reaction of a phosphorus oxytrihalide, which remains unreacted with a bisphenol A derivative, and a hydroxy compound.

Specifically, the monomer-type phosphoric ester is, for example, triphenyl phosphate or isopropenyl phenyl diphenyl phosphate when the bisphenol A derivative is a bisphenol A and the hydroxy compound is a phenol; tricresyl phosphate, phenyl dicresyl phosphate, or isopropenyl phenyl dicresyl phosphate when the hydroxy compound is a cresol [(o-, m-, p-)methylphenol]; and trixylyl phosphate, phenyl dixylyl phosphate, or isopropenyl phenyl dixylyl phosphate when the hydroxy compound is xylenol[(2,3-2,4-, 2,5-, 2,6-, 3,4-, 3,5-)dimethylphenol].

The temperature at which the second step of process 1 is carried out is preferably 60 to 170° C., more preferably 80 to 170° C., still more preferably 120 to 170° C., and especially preferably 140 to 160° C.

The time period for which the second step of process 1 is carried out is preferably 1 hour and 30 minutes to 21 hours, and more preferably 3 hours to 15 hours.

In a preferred embodiment, the amount of the hydroxy compound used is greater by an excess ratio of equal to or less than 2 mol % than the amount which is theoretically necessary for turning the entire amount of the phosphorohalidate contained in the reaction mixture into a condensed phosphoric ester. The "excess ratio" is described later in detail.

The other reaction conditions are appropriately selected as desired. The hydrogen halide generated during the reaction and remaining after the reaction is preferably recovered at normal pressure or low pressure.

Preferred Embodiment of Second Step of Process 1

In a preferred embodiment, at the second step of process 1, a reaction product obtained at the first step and a monophenol-based compound are reacted at the temperature of 120° C. or lower, and thereafter, the temperature is raised to 120° C. or higher, and the phosphorohalidate and a hydroxy compound are reacted.

In this embodiment, a reaction product obtained at the first step of process 1 and a monophenol-based compound are first reacted at the temperature of 120° C. or lower. The temperature for this reaction is preferably equal to or lower than 110° C., more preferably equal to or lower than 105° C., and still more preferably equal to or lower than 100° C.

By adopting such a relatively low temperature, a portion of the monophenol-based compound reacts with the IPP contained in the reaction mixture generated after the first step of process 1. As a result, the IPP is removed.

When the reaction temperature is too high, the monophenol-based compound reacts with the phosphorohalidate with priority, and therefore the reaction of the monophenol-based compound and the IPP is unlikely to sufficiently proceed. Therefore, the amount of the IPP is unlikely to be sufficiently reduced.

The lower limit of the reaction temperature adopted at the second step of process 1 in this embodiment is not specifically determined. Notably, a temperature at which the IPP and the monophenol-based compound can contact each other efficiently without a dehydrohalogenation reaction being caused is preferable. The lower limit of the reaction temperature is appropriately determined based on the combination of the type and amount of the monophenol-based compound, the speed at which the monophenol-based compound is added, the reaction scale, and other reaction conditions (e.g., reaction time, reduction inpressure, whethera solvent is used or not). The lower limit of the reaction temperature is preferably, for example, equal to or higher than 40° C., more preferably equal to or higher than 60° C., still more preferably equal to or higher than 70° C., and especially preferably equal to or higher than 80° C.

The time period during which the second step of process 1 in this embodiment is performed at the reaction temperature of 120° C. or lower is preferably 30 minutes to 8 hours, and more preferably 1 to 6 hours.

According to this embodiment, even when a reaction product after the first step of process 1 contains an isopropenyl aryl group-containing phosphate, the isopropenyl aryl group-containing phosphate can be removed at the second step.

After the above operation of performing the reaction at 120° C. or lower, the temperature is raised to a temperature higher than 120° C., and a phosphorohalidate and a hydroxy compound are reacted, whereby a condensed phosphoric ester can be prepared.

In this embodiment, the reaction temperature of 120° C. or lower is increased to a reaction temperature higher than 120° C., preferably over 30 minutes to 8 hours, and more preferably 1 to 6 hours. Preferably, the reaction temperature is increased up to 120 to 170° C. More preferably, the reaction temperature is increased up to 140 to 160° C. After the reaction temperature has been increased, it is maintained at a temperature higher than 120° C. preferably for 30 minutes to 5 hours, and more preferably 1 to 3 hours. Preferably, the reaction temperature is maintained at 140 to 160° C.

The total amount of the materials used in the second step of process 1 is preferably added before the second step of process 1 is started. When necessary, a portion of the materials can be added during the second step of process 1. For example, a portion of the materials may be added during the reaction performed at 120° C. or lower; a portion of the materials maybe added during the time period when the reaction temperature of 120° C. or lower is increased to the reaction temperature higher than 120° C.; and a portion of the materials may be added during the reaction performed at the reaction temperature higher than 120° C.

The amount of the reactive materials used in the second step of process 1 described in this specification refers to the total amount of the materials added before the completion of the second step of process 1.

The other reaction conditions are appropriately selected as desired. The hydrogen halide generated during the reaction and remaining after the reaction is preferably recovered at normal pressure or low pressure.

In a preferred embodiment, the amount of the hydroxy compound is greater by an excess ratio of equal to or less than 2 mol % than the amount which is theoretically necessary for turning the entire amount of the phosphorohalidate contained in the reaction mixture into a condensed phosphoric ester.

In this embodiment, the production of a monomer-type phosphoric ester as a by-product which is caused by interesterification of the condensed phosphoric ester produced and the hydroxy compound can be suppressed without reducing yield or quality. Considering that interesterification of the condensed phosphoric ester and the hydroxy compound is likely to occur especially in industrial, large scale production due to the long reaction time, using the hydroxy compound in an amount based on the above excess ratio is very advantageous.

Here, the term "industrial scale" indicates that the total amount of the monophenol-based compound and the phosphorohalidate which are reacted with each other is an amount used in usual industrial production. Specifically, industrial scale is preferably equal to or greater than 5 liters, more preferably equal to or greater than 30 liters, still more preferably equal to or greater than 100 liters, and especially preferably equal to or greater than 300 liters.

The total amount of the hydroxy compound and the phosphorohalidate which are reacted with each other is specifically preferably equal to or less than 20000 liters, and more preferably equal to or less than 10000 liters due to restrictions caused by, for example, the reaction apparatus.

When the amount of the hydroxy compound is smaller than the theoretical amount stoichiometrically calculated, unreacted phosphorohalidate will inevitably remain, which is likely to cause problems which complicate the purification and post-processing steps.

When the amount of the hydroxy compound is the theoretical amount stoichiometrically calculated, the reaction is likely to be incomplete. As a result, unreacted phosphorohalidate remains, which is likely to cause the problems of, for example, the phosphorohalidate remaining in the product as an impurity or complicating the purification and post-processing steps.

An excess amount of the monophenol-based compound is not preferable since the amount of the monomer-type phosphoric ester produced as a by-product is increased. Therefore, the monophenol-based compound is preferably greater than the stoichiometrically theoretical amount by equal to or less than 2.0 mol %, more preferably equal to or less than 1.8 mol %, still more preferably equal to or less than 1.6 mol %, and especially preferably equal to or less than 1.5 mol %.

The stoichiometrically theoretical amount necessary for turning the entire amount of the phosphorohalidate into a condensed phosphoric ester refers to the amount which is necessary for substituting all the halogen atoms contained in the phosphorohalidate with arylester groups. For example, in the case where n=1 in formula (I) above, such an amount of the monophenol-based compound is 4 mol with respect to 1 mol of the phosphorohalidate. In the case where n=2, such an amount of the monophenol-based compound is 5 mol with respect to 1 mol of the phosphorohalidate. In the case where n=3, such an amount of the monophenol-based compound is 6 mol with respect to 1 mol of the phosphorohalidate.

Here, the excess ratio is a value obtained by subtracting the stoichiometrically theoretical mol value from the used mol value of the monophenol-based compound, dividing the resultant value by the stoichiometrically theoretical mol value to obtain a ratio, and then multiplying the ratio by 100 so as to be represented by a percentage.

The lower limit of the amount of the monophenol-based compound cannot be exactly determined since it varies in accordance with, for example, the type of the condensed phosphoric ester and the reaction conditions. The lower limit is preferably equal to or greater than 0.2 mol %, more preferably equal to or greater than 0.3 mol %, especially preferably equal to or greater than 0.4 mol %, and still more preferably equal to or greater than 0.5 mol %.

The other reaction conditions (e.g., the reduction in pressure and the time to add the hydroxy compound) are appropriately selected as desired.

The hydrogen halide generated during the reaction and remaining after the reaction is preferably recovered at normal pressure or low pressure. The hydrogen halide can be, for example, captured by water to be recovered.

A condensed phosphoric ester prepared in this manner usually contains a great amount of impurities including partially reacted components, unreacted components, and remaining catalysts. Therefore, the impurities are removed from the crude condensed phosphoric ester by known purification methods such as neutralization, water rinsing, steam distillation or the like.

When, for example, a method using an epoxy compound is adopted for purification, the epoxy compound is added to an —OH group of a partially reacted component and then selective hydrolysis is performed. Thus, the partially reacted product can be converted into phosphoric acid. By washing the phosphoric acid with hot water, the phosphoric acid components can be removed so as to reduce the acid value of the product.

A product obtained in this manner is a high quality condensed phosphoric ester having a very low content of monomer-type phosphoric ester.

As described above, most preferably, at the first step of process 1, a bisphenol A derivative and a phosphorus oxytrihalide are reacted so as to generate a phosphorohalidate, and an unreacted phosphorus oxytrihalide is removed from the reaction product. Then, at the second step, the reaction product obtained at the first step and a monophenol-based compound are reacted at the temperature of 120° C. or lower. Thereafter, the temperature is raised to 120° C. or higher, and the phosphorohalidate and a hydroxy compound are reacted at the temperature of 120° C. or higher, whereby a monomer-type phosphoric ester can be reduced most efficiently.

Such a high quality condensed phosphoric ester can be used for various types of resins as a flame retardant.

Specifically, the high quality condensed phosphoric ester can be used for, for example, the following resins: thermoplastic resins such as polyethylene-based resins, polypropylene-based resins, polybutadiene-based resins, polystyrene-based resins, polyphenylene ether-based resins, polycarbonate-based resins, ABS (acrylonitrile-butadiene-styrene)-based resins, high impact styrene-based resins, SAN (styrene-acrylonitrile)-based resins, polyamide-based resins, polyester-based resins, polyphenylene sulfide-based resins, polyacrylic resins, polymethacrylic resins, and the like; and thermosetting resins such as epoxy-based resins, polyurethane-based resins, polyimide-based resins, phenol-based resins, novolac-based resins, polyetherimide-based resins, melamine-based resins, urea-based resins and the like.

A condensed phosphoric ester obtained by a method of the present invention can be especially advantageously used for a resin having a high molding temperature, for example, a resin moldable at a temperature of equal to or higher than 160° C. in one embodiment, a resin moldable at a temperature of equal to or higher than 180° C. in a more preferable embodiment, and a resin moldable at a temperature of equal to or higher than 200° C. in an especially preferable embodiment.

When a condensed phosphoric ester obtained by a method of the present invention is added to any of the above-listed resins as a flame retardant, a high quality molded product having excellent resistance against heat and resistance against coloring can be obtained without generating gas, despite the high process temperature during the molding process of the resin, using a molding apparatus.

A condensed phosphoric ester obtained by a method of the present invention is added to a resin and molded. As result, any desired flame retardant molded product is provided.

For adding the flame retardant to the resin and for molding the resin supplied with the flame retardant, any known method is usable.

For example, the components (e.g., the resin, flame retardant, plasticizer, flame-retarding adjuvant, releasing agent, ultraviolet absorbing agent, anti-oxidant, light-shielding agent, weather resistance improving agent, and inorganic filler) can be melted and kneaded using a multi-purpose kneading apparatus such as a single-screw extruder, a twin-screw extruder, a Banbury mixer, a kneader, a mixer, a roll or the like and mixed with each other. Alternatively, a molding apparatus such as an extruding molding apparatus can be used to produce a plate-like, sheet-like, or film-like molded product. Thus, a desired molded product is obtained.

Process 2

Next, above process 2 is described. In process 2, the following steps are performed:

A first step of reacting a phosphorus oxytrihalide with a hydroxy compound in the presence of a decomposition retardant; and A second step of reacting an obtained reaction product with a bisphenol A derivative.

When necessary, a step of distilling a diphenyl phosphorochloride may be provided between the first step and the second step of process 2.

As the conditions for the first step of process 2, the conditions adopted in a conventionally known method for preparing a condensed phosphoric ester may be adopted. Preferably, the first step of process 2 is performed at the temperature of 40° C. to 130° C. For the conditions other than temperature, for example, substantially the same conditions as those employed for the second step of process 1 are usable.

As the conditions for the second step of process 2, the conditions adopted in a conventionally known method for preparing a condensed phosphoric ester may be adopted. Preferably, the second step of process 2 is performed at the temperature of 120° C. to 150° C. For the conditions other than temperature, for example, substantially the same conditions as those employed for the first step of process 1 are usable.

As materials that can be used in this process, materials adopted in a conventionally known method for preparing a condensed phosphoric ester may be adopted. For example, the same materials as those used in process 1 described above may be used.

In process 2, the decomposition retardant may not be removed after preparation of a condensed phosphoric ester so as to be left in a condensed phosphoric ester product. However, in the case where in view of the quality of an intended condensed phosphoric ester product, the decomposition retardant should not be left in the condensed phosphoric ester product, or the amount of the decomposition retardant left in the condensed phosphoric ester product should be equal to or smaller than a certain amount, a step of removing the decomposition retardant may be provided. In this case, a method for removing the decomposition retardant is realized by any method. For example, filtration, decantation, or the like, may be employed. A preferable time for removing the decomposition retardant is the time after the second step of process 2.

Process 3

Next, above process 3 is described. In process 3, the following step is performed: A step of simultaneously reacting a bisphenol A derivative, a phosphorus oxytrihalide, and a hydroxy compound in the presence of a decomposition retardant.

As for the reaction conditions for process 3, the conditions adopted in a conventionally known method for preparing a condensed phosphoric ester may be adopted. For example, the reaction may be caused at the temperature of 40° C. to 170° C.

As materials that can be used in this process, materials adopted in a conventionally known method for preparing a condensed phosphoric ester may be adopted. For example, the same materials as those used in process 1 described above may be used.

In process 3, the decomposition retardant may not be removed after preparation of a condensed phosphoric ester so as to be left in a condensed phosphoric ester product. However, in the case where in view of the quality of an intended condensed phosphoric ester product, the decomposition retardant should not be left in the condensed phosphoric ester product, or the amount of the decomposition retardant left in the condensed phosphoric ester product should be equal to or smaller than a certain amount, a step of removing the decomposition retardant may be provided. In this case, a method for removing the decomposition retardant is realized by any method. For example, filtration, decantation, or the like, may be employed. A preferable time for removing the decomposition retardant is the time after the reaction of a bisphenol A derivative, a phosphorus oxytrihalide, and a hydroxy compound has been completed.

EXAMPLES

Hereinafter, non-limiting examples of the present invention will be described, but the present invention is not limited to these examples.

In the examples, the content of the monomer-type phosphoric ester in each product was measured by high-performance liquid chromatography (device: LC10AD produced by Shimadzu Corporation, column: SilicaODS-80TM, oven: CTO-10A, eluant: methanol:water=8:2 (v/v), flow rate: 0.8 ml/min., detector: SPD10A, UV frequency of the detector: 254 nm). In the examples, "%" represents "% by weight" unless otherwise specified.

Example 1

A 1 liter reaction device including a stirrer, a thermometer, a dripper, a hydrochloric acid recovery device and a condenser (30° C.) was filled with 552.6 g (3.6 mol) of phosphorus oxychloride, 228.4 g (1 mol) of bisphenol A, 2.3 g of magnesium chloride, 0.38 g of BHT, and 0.5 g of stannic oxide (0.22 parts by weight with respect to 100 parts by weight of a bisphenol A derivative). These materials were heated to 105° C. over 2 hours while being stirred, and then reacted for another 3 hours. Hydrochloric acid generated was recovered by the hydrochloric acid recovery device (amount recovered: 71.0 g).

Then, unreacted phosphorus oxychloride (243.0 g) was recovered at a temperature of 160° C. and a pressure of 350 mmHg in a nitrogen atmosphere. The concentration of chlorine in the resultant reaction product was 30.0%. 368.9 g (excess ratio: 1%) of phenol was added to 459.8 g of the resultant reaction product over 3 hours at 100° C. and normal pressure, then the temperature was raised to 150° C. over 2 hours, and the reaction was continued for another 1 hour for aging. Hydrochloric acid generated was recovered by the hydrochloric acid recovery device (amount recovered: 125.6 g). Then, the hydrochloric acid remaining in the system was completely removed at 150° C. and 10 mmHg over 1 hour. Thus, 681.3 g of crude condensed phosphoric ester was obtained.

The crude condensed phosphoric ester was diluted with toluene and then washed with an aqueous solution of diluted hydrochloric acid. Then, the organic phase containing the crude condensed phosphoric ester was treated with propylene oxide. After the resultant substance was repetitively rinsed with water, toluene was recovered by distillation under reduced pressure. Then, unreactedphenol was removed by steam distillation. As a result, 680 g of condensed phosphoric ester containing 85.6% of a compound represented by general formula (II) where n=1 (2,2-bis{4-[bis(phenoxy)phosphoryl]oxyphenyl}propane), 12.5% of a compound represented by general formula (II) where n=2, and 2.0% of a compound represented by general formula (II) where n=3, was obtained. The content of the monomer-type phosphoric ester in the resultant product was 0.9%, and the acid value (KOH/mg) thereof was 0.04.

Example 2

The same operation as that of example 1 was performed, except that 0.5 g of ascorbic acid was used in place of stannic oxide. The content of the monomer-type phosphoric ester in the resultant product was 2.0%, and the acid value (KOH/mg) thereof was 0.06.

Comparative Example 1

The same operation as that of example 1 was performed, except that stannic oxide was not used. The content of the monomer-type phosphoric ester in the resultant product was 4.2%, and the acid value (KOH/mg) thereof was 0.04.

Example 3

The same operation as that of example 1 was performed, except that cupric chloride was used in place of stannic oxide. The content of the monomer-type phosphoric ester in the resultant product was 2.9%, and the acid value (KOH/mg) thereof was 0.06.

Example 4

The same operation as that of example 1 was performed, except that ferric chloride was used in place of stannic oxide. The content of the monomer-type phosphoric ester in the resultant product was 2.4%, and the acid value (KOH/mg) thereof was 0.07.

Example 5

The same operation as that of example 1 was performed, except that adipic acid was used in place of stannic oxide. The content of the monomer-type phosphoric ester in the resultant product was 2.0%, and the acid value (KOH/mg) thereof was 0.09.

Example 6

The same operation as that of example 1 was performed, except that oxalic acid was used in place of stannic oxide. The content of the monomer-type phosphoric ester in the resultant product was 2.7%, and the acid value (KOH/mg) thereof was 0.06.

Example 7

The same operation as that of example 1 was performed, except that citric acid was used in place of stannic oxide. The content of the monomer-type phosphoric ester in the resultant product was 2.4%, and the acid value (KOH/mg) thereof was 0.05.

INDUSTRIAL APPLICABILITY

Effect of the Invention

In a condensed phosphoric ester prepared by the present invention, the content of the monomer-type phosphoric ester resulting from decomposition of a bisphenol A derivative can be reduced without reducing the yield of the products. Further, by settings conditions, a condensed phosphoric ester which does not substantially contain a monomer-type phosphoric ester can be obtained. Accordingly, a condensed phosphoric ester prepared by the method of the present invention is excellent in heat resistance, volatility and coloring resistance. When used as a plasticizer or a flame retardant for a resin, the condensed phosphoric ester prepared by the method of the present invention has the advantages of preventing generation of hazardous gas and the contamination of the molds during the molding, and reduction in the heat resistance of the molded product. Among these advantages, improved prevention of the contamination of the molds is industrially especially advantageous since it increases the number of continuous shots and thus reduces the production costs.

What is claimed is:

1. A method for preparing a condensed phosphoric ester, comprising a process of reacting a bisphenol A derivative, wherein
   the bisphenol A derivative refers to bisphenol A or a derivative thereof, which is represented by the following formula (A):

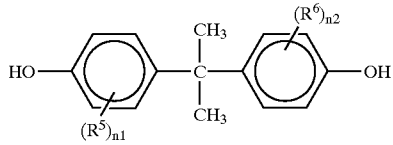

(A)

where $R^5$ and $R^6$ are the same or different from each other and represent an alkyl group containing 1 to 3 carbon atoms; and n1 and n2 each represent an integer from 0 to 4,
a phosphorus oxytrihalide, and a hydroxy compound in the presence of a decomposition retardant.

2. A method according to claim 1, wherein the decomposition retardant is an organic carboxylic acid-based compound.

3. A method according to claim 2, wherein the organic carboxylic acid-based compound is ascorbic acid or adipic acid.

4. A method according to claim 1, wherein the decomposition retardant is an oxide or chloride of tin, copper, or iron.

5. A method according to claim 4, wherein the oxide or chloride of tin, copper, or iron is a stannic oxide, a ferric chloride, or a cupric chloride.

6. A method according to claim 1, wherein the amount of the decomposition retardant used is 0.01–5 parts by weight with respect to 100 parts by weight of the bisphenol A derivative.

7. A method according to claim 1, wherein the process of reacting a bisphenol A derivative, a phosphorus oxytrihalide, and a hydroxy compound includes:
   a first step of reacting the bisphenol A derivative and the phosphorus oxytrihalide so as to produce a phosphorohalidate; and
   a second step of reacting the phosphorohalidate and the hydroxy compound.

8. A method according to claim 1, wherein the process of reacting a bisphenol A derivative, a phosphorus oxytrihalide, and a hydroxy compound includes:
   a first step of reacting the bisphenol A derivative and the phosphorus oxytrihalide so as to produce a phosphorohalidate, and removing unreacted phosphorus oxytrihalide from a reaction product; and
   a second step of reacting the phosphorohalidate and the hydroxy compound.

9. A method according to claim 7, wherein the amount of the hydroxy compound used is greater by equal to or less than 2 mol % than an amount which is theoretically necessary for turning the entire amount of the phosphorohalidate into a condensed phosphoric ester.

10. A method according to claim 1, wherein the process of reacting a bisphenol A derivative, a phosphorus oxytrihalide, and a hydroxy compound includes:
    a first step of reacting the bisphenol A derivative and the phosphorus oxytrihalide so as to produce a phosphorohalidate; and
    a second step of reacting a reaction product obtained at the first step and a monophenol-based compound at the temperature of 120° C. or lower, and thereafter, increasing the temperature to 120° C. or higher, and reacting the phosphorobalidate and a hydroxyl compound.

11. A method according to claim 1, wherein the process of reacting a bisphenol A derivative, a phosphorus oxytrihalide, and a hydroxy compound includes:
    a first step of reacting the bisphenol A derivative and the phosphorus oxytrihalide so as to produce a phosphorohalidate, and removing unreacted phosphorus oxytrihalide from a reaction product; and
    a second step of reacting a reaction product obtained at the first step and a monophenol-based compound at the temperature of 120° C. or lower, and thereafter, increasing the temperature to 120° C. or higher, and reacting the phosphorohalidate and a hydroxyl compound.

12. A method according to claim 1, wherein the condensed phosphoric ester is 2,2-bis{4-[bis(phenoxy) phosphoryl]oxyphenyl}propane.

* * * * *